(12) United States Patent
Jacobson et al.

(10) Patent No.: US 6,924,299 B2
(45) Date of Patent: Aug. 2, 2005

(54) METHODS AND COMPOSITIONS USEFUL IN ENHANCING OXYGEN DELIVERY TO CELLS

(75) Inventors: Elaine L. Jacobson, Tucson, AZ (US); Myron K. Jacobson, Tucson, AZ (US); Jaber G. Qasem, Tucson, AZ (US); Hyuntae Kim, Tucson, AZ (US); Moonsun Kim, Tucson, AZ (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/834,228

(22) Filed: Apr. 12, 2001

(65) Prior Publication Data

US 2002/0034482 A1 Mar. 21, 2002

Related U.S. Application Data

(60) Provisional application No. 60/197,227, filed on Apr. 14, 2000.

(51) Int. Cl.$^7$ ............................................. A61K 33/44
(52) U.S. Cl. ....................................................... 514/356
(58) Field of Search .......................................... 514/356

(56) References Cited

U.S. PATENT DOCUMENTS

| 2,431,558 A | * | 11/1947 | Huber |
| 4,847,260 A | * | 7/1989 | Abe et al. |
| 5,151,271 A | * | 9/1992 | Otsuka et al. |
| 5,738,879 A | * | 4/1998 | Rine |

OTHER PUBLICATIONS

Shargel et al., Applied Biophaceutics and Pharmacokinetics, 3rd ed., 1993, pp. 77–83.*

Remington's Pharmaceutical Sciences, $18^{th}$ ed., 1990, p. 1680.*

Le et al., International Journal of Pharmaceutics, 1998; 163: 11–22.*

* cited by examiner

Primary Examiner—San-Ming Hui
(74) Attorney, Agent, or Firm—Fulbright & Jaworski LLP

(57) ABSTRACT

The invention discloses compositions and methods which are useful in improving delivery of oxygen to cells. The compositions require at least one derivative of a compound. The derivatives are chosen to have log P values below about 6.0.

11 Claims, 4 Drawing Sheets

METHODS AND COMPOSITIONS USEFUL IN ENHANCING OXYGEN DELIVERY TO CELLS

RELATED APPLICATION

This application claims priority of provisional application Ser. No. 60/197,227, filed Apr. 14, 2000, incorporated by reference.

FIELD OF THE INVENTION

This invention relates to methods that are useful in improving the delivery of oxygen to tissues and organs, such as skin. Therapeutic uses of the method are disclosed as well.

BACKGROUND AND PRIOR ART

The skin plays multiple roles in protection from environmental insults. Environmental exposure results in the progressive deterioration of skin that is initially cosmetic but can lead to end stage diseases such as actinic keratosis and skin cancer. Hereinafter, while the skin will be discussed specifically, it is to be understood that the remarks are applicable to organs and tissues in general.

Health of skin, as well as other tissues and organs, is dependent upon supplies of many essential nutrients to cellular components which are a part thereof, oxygen in particular, as well as the efficient removal of waste products such as carbon dioxide, and other metabolic end products. An optimal supply of oxygen is required in order to support metabolic pathways which inter alia, support the cellular mechanisms that lead to resistance of skin deterioration.

The delivery of oxygen to skin via blood circulation is distal to delivery to most other organs. Further, the uppermost living layer of skin, i.e., the "epidermis," is non-vascular. This leaves the upper layers of skin at high risk of receiving insufficient oxygen.

Skin is a complex organ system, consisting of multiple layers. The uppermost, or "stratum corneum" layer, consists of non-living material derived primarily from the terminal differentiation of epidermal keratinocytes, and provides a protective barrier for the underlying components of skin. The epidermis contains a number of cell types, although keratinocytes are the major cell type. Dermal fibroblasts are embedded within a matrix comprised of collagen, elastin, proteoglycans, and other extracellular matrix molecules. Blood capillaries are found in the dermis, but the epidermis is non-vascular.

As people age, progressively deleterious changes in skin appearance occur. The initial changes are the loss of smooth skin texture and the appearance of age spots, followed by changes in elasticity that lead to the appearance of skin wrinkles. The age at which these changes appear and the rate at which one stage progresses to the next varies greatly from individual to individual. During the normal aging process, both the epidermis and dermis become thinner with a loss of cell numbers and connective tissue, leading to the appearance of fine wrinkles. Ultraviolet (UV) irradiation from the sun causes photodamage that accelerates skin deterioration. In contrast to the thinning observed in sun-protected skin, photodamaged skin has a thickened and rough appearance with an increase in deeper skin wrinkling which occurs in dermal tissue. Photodamage also causes end-stage skin deterioration including pre-malignant lesions termed actinic keratosis and skin cancer.

Compelling evidence now indicates that oxidative stress, defined as an abnormal accumulation of reactive oxygen species (ROS hereafter) is involved in the pathophysiology of skin deterioration. ROS include, inter alia, superoxides, the hydroxyl radical, hydrogen peroxide, singlet oxygen, nitric oxide, peroxynitrite, and hypochlorite. See, e.g., Simonian, et al., Ann. Rev. Pharmacol. Toxicol. 36:83–106 (1996), incorporated by reference. All cells are exposed to ROS during the normal course of energy metabolism, via environmental exposure and/or immune surveillance. While ROS are involved in normal cell signaling pathways, elevation of ROS during oxidative stress disrupts signaling pathways, often resulting in cell death by apoptosis or necrosis. Thus, it is likely that ROS are involved in the decrease in cell number observed over time, even in sun-protected skin.

Exposure to the ultraviolet rays of sunlight is a major source of skin oxidative stress. Two major targets for damage by ROS in skin are DNA and protein. DNA damage is of particular interest in that unrepaired damage can lead to the loss of skin cells and to altered functioning of cells that survive genotoxic stress.

While some changes in skin during aging can not be avoided, much skin deterioration at an early age is avoidable. Skin cells contain a number of protective mechanisms for the prevention and repair of ROS damage to DNA and protein. For example, a number of intracellular molecules, including glutathione and the antioxidant vitamins C and E play key roles in scavenging ROS before they can react with cellular macromolecules. Indeed, the antioxidant vitamins have already found application in the prevention of skin deterioration, as they are components of many skin creams. Also, cells contain complex mechanisms for the maintenance of genomic integrity. Of particular interest herein is the accumulating evidence for the involvement of DNA repair mechanisms in maintaining the genomic integrity of organs and tissues subjected to genotoxic stress caused by, e.g., ROS, including skin.

The delivery of oxygen is important for proper maintenance of cell energy metabolic pathways, which in turn is important for alleviating the problems discussed herein. It is desirable to have a method available by which oxygen delivery to a tissue or organ, such as the skin, can be improved. Hence, one object of the invention is a method for improving delivery of oxygen to tissues and organs, such as skin. Yet a further aspect of the invention are compositions useful in achieving this goal. Still a further aspect of the invention is the treatment of conditions where improved oxygenation is called for, via application of the methods and compositions of the invention.

How these aspects of the invention are met will be seen from the disclosure which follows.

DETAILED DESCRIPTION OF PREFERRED EMBODIMENTS

Figure 1:
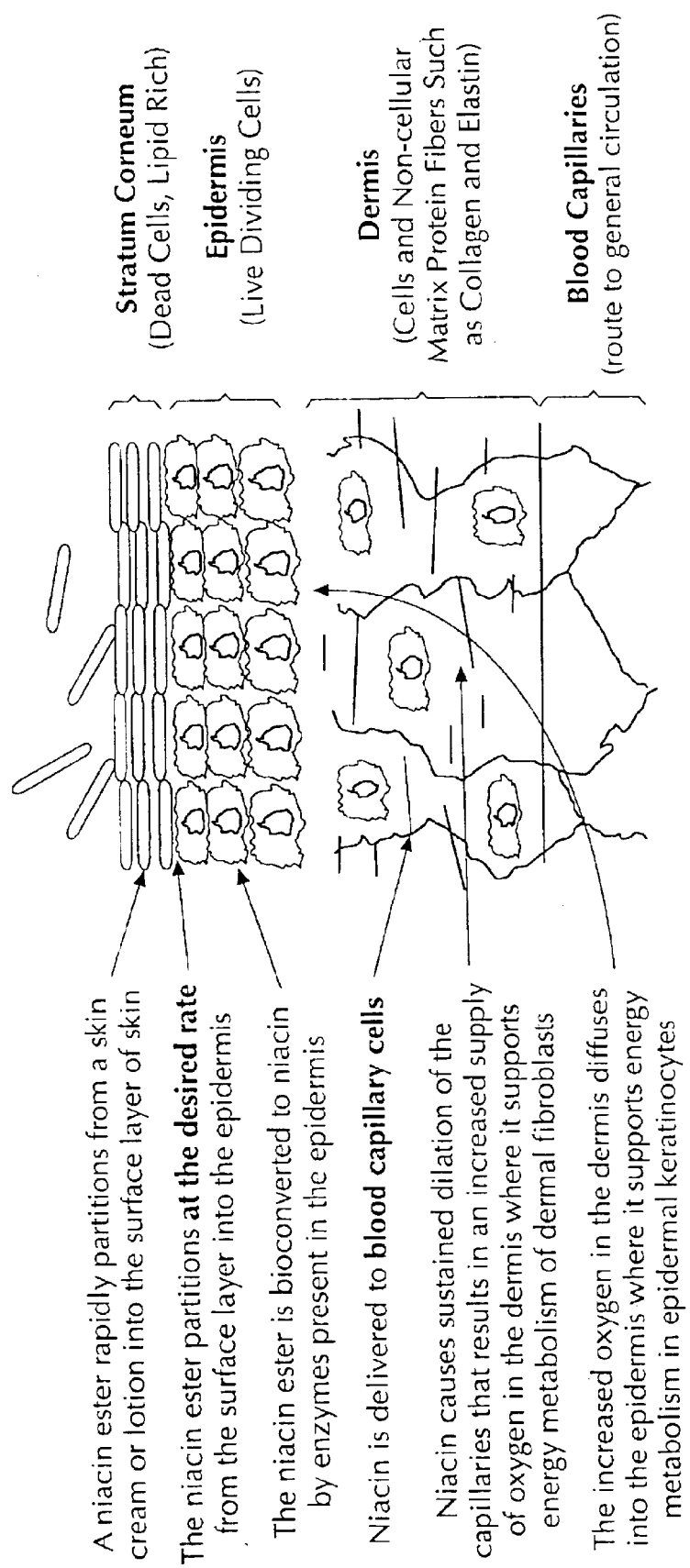
FIG. 1 depicts the skin, in cross section, in combination with an illustration of the delivery system of the invention.

The invention described herein involved various formulations designed to enhance delivery of oxygen to tissues and organs, such as the skin. The compositions are formulated so as to partition rapidly into a layer, such as the stratum corneum layer of the skin, at a rate which permits sustained delivery of an active agent or agents to, e.g., the epidermis, in a sustained fashion and at a concentration which provokes capillary dilation. As a result of capillary dilation, blood flow increases, thereby increasing oxygen tension in the dermis which in turn supports both energy metabolism in epidermal fibroblasts, and epidermal keratinocytes when the skin is involved, and other parallel cell types when other tissues and/or organs are involved.

The highly lipophilic nature of the stratum corneum dictates that the desired oxygen enhancing agent must be sufficiently lipophilic to effectively partition into the stratum corneum from the donor compartment, which may be, e.g., a skin cream or lotion. This necessitates the preparation of a distinct lipophilic agent, such as those described in more detail infra. Diffusion from the stratum corneum into the epidermis also requires that the agent should be sufficiently lipophilic to rapidly partition from the cream or lotion into the stratum corneum. Niacin esters are exemplified herein. Lipophilic derivatives of niacin esters can be prepared, and these are converted into active niacin esters following diffusion out of the stratum corneum into the epidermis; however, other materials could also be used. The lipophilicity of the agent should allow it to be formulated in, e.g., skin cream or lotion and the ester linkage should be very stable in these formulations to, e.g., chemical hydrolysis under aqueous conditions.

The experiments which follow set forth the invention in greater detail, but should not be construed as limiting the invention in any way.

EXAMPLE 1

Nicotinic acid esters were synthesized in accordance with Ser. No. 09/452,617, filed Dec. 1, 1999, incorporated by reference. In brief, nicotinoyl chloride was combined with triethylamine (TEA), dimethylaminopyridine (DMAP), and various alkyl alcohols, under nitrogen. Esters resulting from the synthesis were separated via silica gel column chromatography, and converted to HCl salts for further purification, using standard methods. The purity was confirmed via thin layer chromatography, and $^1$H-NMR.

The $P_{oct/w}$ values for these compounds were determined in accordance with Harnisch, et al., J. Chromatog. 282:315–332 (1983), incorporated by reference. This reference also describes determination of "log P" values, described infra.

EXAMPLE 2

This example details the first of two sets of experiments designed to determine the vasodilation effect of alkyl niacin esters. Formulations were prepared by combining the alkyl esters referred to supra in a skin lotion, at 0.1% and 1.0% concentrations. The lotions were applied topically to the skin of human volunteers on the anterior surface of a forearm. Vasodilation was observed visually, i.e., by observing blushing at the site of application, or lack thereof. Both onset and duration of vasodilation were measured.

The results for the esters tested are set forth in Table 1, which follows. This table includes lipophilicity of the tested compounds, in log P values, following Harnisch, et al., supra, incorporated by reference, as well as the results of visual observation.

It will be seen that small chain alkyl esters, i.e., those with 8 carbon atoms or less in the alkyl chain, caused vasodilation at concentrations as low as 0.1%, while C9 and C10 alkyl esters caused vasodilation at 1.0% formulations. The longer chain esters, i.e., those at C12 or higher, did not provoke vasodilation at either concentration.

The onset and duration of vasodilation was determined, again by visual determination, for C2, C6, and C8 alkyl esters. Results are set forth in Table 2. Note that the log P values provided for the C9 and C11 compounds are derived from a plot of experimentally determined values for other compounds. The C8 compound provided the longest effect. Thus, niacin esters with log P values of less than 6.0 are preferred. Most preferred are esters with log P values in the range of from about 4.5 to about 5.5.

TABLE 1

Properties of Niacin Esters

| Alkyl Carbon Chain Length | Log P Value* | Vasodilation at 0.1% | Vasodilation at 1.0% |
|---|---|---|---|
| 1 carbon | 0.84 | Yes | Yes |
| 2 carbons | 1.3 | Yes | Yes |
| 4 carbons | 2.4 | Yes | Yes |
| 6 carbons | 3.5 | Yes | Yes |
| 8 carbons | 4.8 | Yes | Yes |
| 9 carbons | 5.0* | No | Yes |
| 10 carbons | 5.8 | No | Yes |
| 11 carbons | 6.0* | No | Slight |
| 12 carbons | 6.6 | No | No |
| 13 carbons | 7.5 | No | No |
| 14 carbons | 7.6 | No | No |
| 15 carbons | 8.3 | No | No |
| 16 carbons | 9.2 | No | No |
| 18 carbons | 9.7 | No | No |

TABLE 2

Vasodilation Properties of Selected Niacin Esters

| Niacin Ester | Vasodilation Effect at 0.1% | |
|---|---|---|
| | Onset | Duration |
| Ethyl niacin | 5–10 min | 30–45 min |
| Hexyl niacin | 10–15 min | 60–90 min |
| Octyl niacin | 10–20 min | 240–360 min |

EXAMPLE 3

The experiments reported in Table 1 reveal compounds that provide sustained vasodilation following topical application; however, they do not indicate whether the vasodilation effect is accompanied by an increased release of oxygen into the skin tissue. To examine this issue, the oxygen content of skin to which the octyl ester discussed supra was determined directly, using a transcutaneous oxygen monitor. The 1% formulation of the octyl ester was applied to skin for 30 minutes. After this thirty minute period, the skin was cleaned with soap and water, wiped with an alcohol swab, and a drop of deionized water was placed on the sensor surface before its attachment to the anterior surface of the volunteers' forearms. The transcutaneous values were recorded constantly, and stored by the instrument. The monitor measures relative oxygen content, because the temperature at which the monitor operates does impact the oxygen permeability of the stratum corneum. See, e.g., Martin, Resp. Care 35:577–589 (1990), incorporated by reference. The sensor was calibrated at 4 hour intervals, or whenever the sensor temperature was changed.

Figure 2:
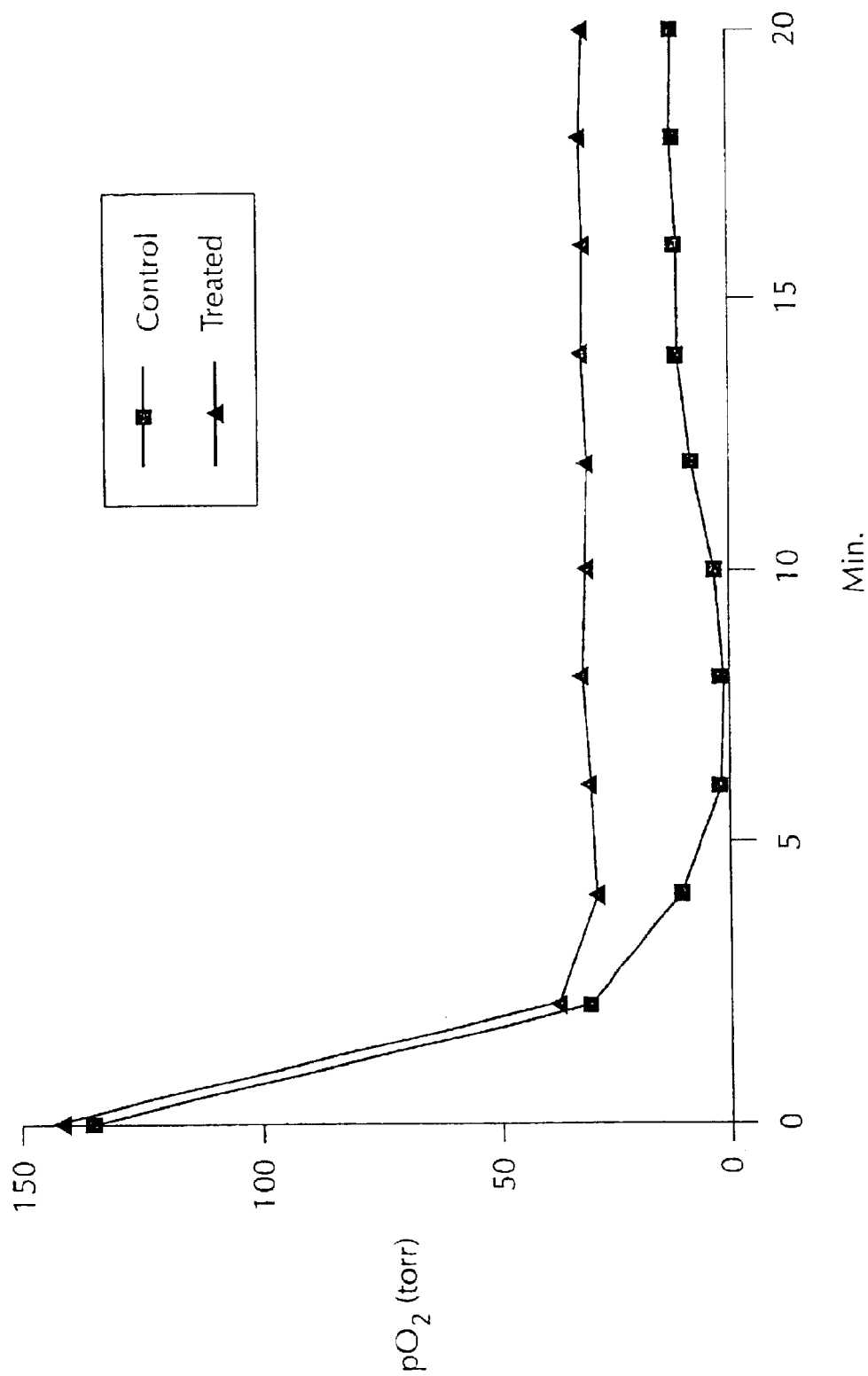
FIG. 2 depicts data obtained in accordance with the invention, via the use of a transcutaneous oxygen monitor.

The results of one set of experiments are presented in FIG. 2. The monitor was operated at a temperature of 40° C. Values are given for both a control, and the formulation described herein.

The first, high value is representative of oxygen tension of air in the monitor probe at the time of application, and then drops rapidly to a very low value, demonstrating low skin oxygen content. This was followed by an increase and a plateau, which is attributed to the effect of simply operating the monitor at 40° C. The depicted results then show a sustained increase in skin oxygen as a result of application of the niacin ester. Comparison of the results for the control and the test compound show a clear increase in the amount of oxygen being delivered to the capillaries.

Figure 3:
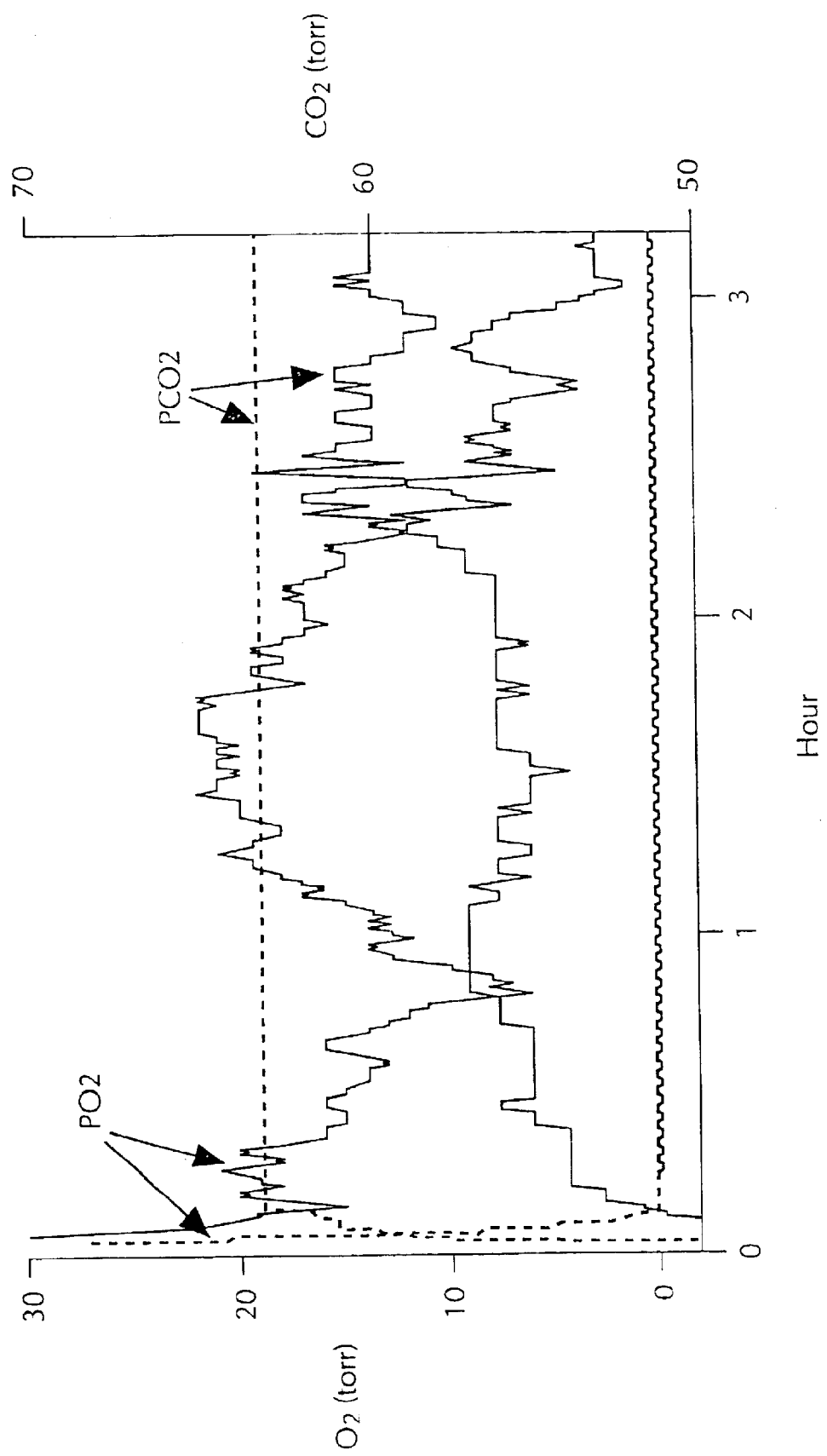
FIG. 3 shows results from a further experiment, using the transcutaneous oxygen monitor.

In a follow-up experiment, the monitor was operated at 38° C., and both $O_2$ and $CO_2$ were measured, with a combined transcutaneous oxygen and $CO_2$ monitor. FIG. 3 presents these results. The control is represented by the dotted line. The results show a sustained increase in skin oxygen content, and a decrease in $CO_2$ content as a result of the application of the niacin ester. The latter result indicates that the topical application is also enhancing removal of metabolic products. While the results of skin oxygen and $CO_2$ measurements are consistent with the observed vasodilation reported in Table 1, observation of vasodilation alone does not necessarily indicate an increased release of oxygen into the skin tissue; however, the results disclosed in FIGS. 2 and 3 demonstrate that application of the niacin esters effects both increased blood flow into skin and increased release of oxygen into the skin.

EXAMPLE 4

Figure 4:
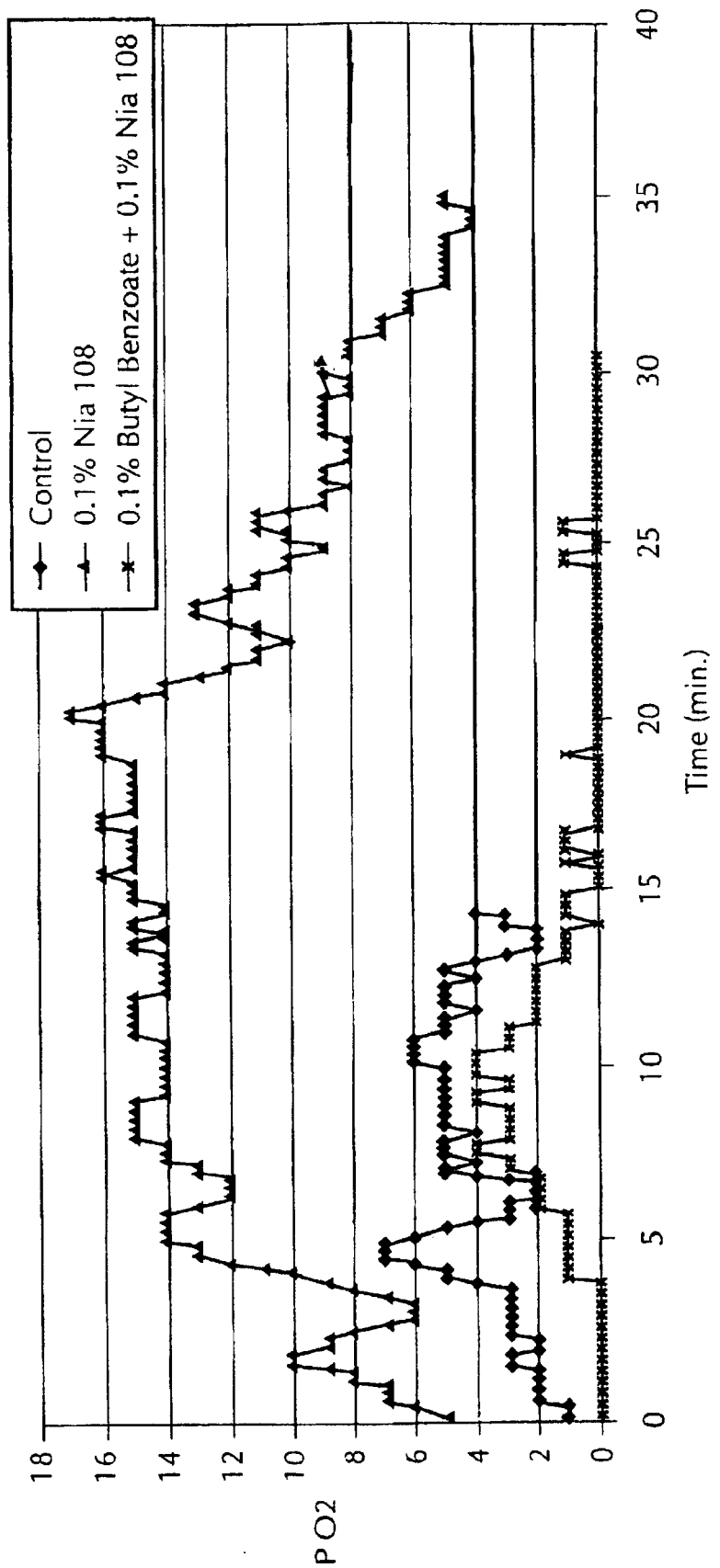
FIG. 4 shows data from an experiment showing that niacin esters are converted to niacin in order to improve skin oxygenation.

Previous work by Sugibayashi, et al., J. Controlled Release 62:201–208 (1999) has shown that, with respect to skin, there is little or no esterase activity in the stratum corneum, the epidermis has highest activity, and the dermis has reduced activity relative to the epidermis. As such, experiments were undertaken to determine if esters require conversion to other molecules in order to provoke oxygenation. An experiment demonstrating that niacin esters require conversion to niacin in order to achieve skin oxygenation is shown in FIG. 4. Parallel experiments were carried out using 0.1% octyl niacin ester lotion, and a lotion containing octyl niacin ester (0.1%), and 0.1% butyl benzoate. Butyl benzoate has a log P value of 3.5, as compared to a value of 4.8 for the octyl ester, suggesting faster partitioning into the epidermis. The presence of the inactive ester, i.e., butyl benzoate, blocked the increase in oxygen content, demonstrating that the conversion of niacin ester to niacin is required. This also shows that inactive co-esters can be used the modulate the oxygenation effect.

Oxygen content was measured in the same way as is described, supra, or using other techniques known to the art.

The foregoing examples describe the invention, which relates to methods and compositions for increasing oxygen delivery to cells. Briefly, these require the use of a derivative of a vasodilator compound, wherein the derivative has a structure such that improved permeation of the vasodilator compound is achieved. In the case of niacin, esters are preferred. Any ester which is a substrate for an indigenous esterase may be used, and is a part of the invention. Especially preferred is the octyl ester of niacin. Especially preferred are esters which have log P values, as described supra, which are lower than about 6.0, more preferably from about 4.5 to about 5.5.

Also a part of the invention is the use of esterified, alcohol analogs of nicotinic acids, wherein the ester group contains from 6 to 12 carbon atoms, preferably 8 to 10, and most preferably 8 carbon atoms. Such molecules also function in the way the niacin esters function. Alcohol analogs of niacin cause vasodilation, and the ester derivatives act in the same way as the ester described supra.

"Derivative" as used herein refers to any chemical modification of the base, vasodilator compound which results in a molecule with the permeation qualities described supra, e.g., a log P values below about 6.0 Esters of compounds such as acid and alcohol esters, are exemplary of such molecules, but are not the only such compounds.

The active ingredient may be applied in any of the standard, topical formulations well known to the art, such as creams, lotions, salves, balms, roll-on sticks, shampoos, washes, suppositories, and so forth. The amount of the active composition in the formulation will vary. Preferably, however, the concentration will range from about 0.05% to about 5.0% by weight. Most preferably, the formulation is one where the ester concentration ranges from about 0.1% by weight to about 1.0% by weight.

These formulations are useful in the treatment of conditions where improved or enhanced oxygenation of tissue is desirable. Such conditions will be well known to the skilled artisan.

Enhanced oxygenation, as discussed supra, enhances other processes within the organ. Hence, a further feature of the invention is the use of the formulations, described supra, in combination with materials such as nutrients, micronutrients, pharmaceutical agents, and other materials where enhanced oxygen delivery will improve the efficacy of the additional material. Of particular interest are compounds and formulations, such as nicotinic acid esters which have log P values in the range described, supra. The art is familiar with how to determine the log P values, as was shown via the citation to, e.g., Harnisch, et al., supra and need not be reiterated here. Similarly, a methodology is set forth herein which shows the skilled artisan how to determine if a particular compound, such as a nicotinic acid ester, increases and/or improves oxygenation. Alkyl esters of nicotinic acid have been described herein; however, other materials, including other nicotinic acid esters can be used as well, as long as they satisfy the criteria that are adduced herein.

Other aspects of the invention will be clear to the skilled artisan and need not be set forth herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A method for enhancing delivery of oxygen to a tissue, comprising administering to said tissue a nicotinic acid alkyl ester containing composition, wherein the alkyl group of said nicotinic acid alkyl ester consists of from 8 to 10 carbon atoms, wherein said composition contains from about 0.05% to about 5.0% by weight of said compound, in an amount sufficient to enhance oxygen delivery to said tissue.

2. The method of claim 1, wherein said nicotinic acid alkyl ester is applied topically.

3. The method of claim 1, wherein said tissue is skin.

4. The method of claim 1, wherein said nicotinic acid alkyl ester is nicotinic acid octyl ester.

5. The method of claim 1, wherein said composition contains from about 0.1% to about 1% by weight of said compound.

6. The method of claim 1, wherein said composition is a cream, a lotion, a salve, a balm, a roll-on stick, a wash, or a suppository.

7. The method of claim 1, wherein said composition further comprises butyl benzoate in an amount sufficient to modulate oxygenation by inhibiting conversion of said nicotinic acid alkyl ester to nicotinic acid.

8. The method of claim 1, wherein said alkyl group of said nicotinic acid alkyl ester consists of 8 carbon atoms.

9. The method of claim 1, wherein said alkyl group of said nicotinic acid alkyl ester consists of 9 carbon atoms.

10. The method of claim 1, wherein said alkyl group of said nicotinic acid alkyl ester consists of 10 carbon atoms.

11. The method of claim 1, wherein said composition enhances delivery of oxygen for at least 4 hours.

* * * * *